United States Patent [19]

Kruse

[11] Patent Number: 5,435,316

[45] Date of Patent: Jul. 25, 1995

[54] LOW AMPLITUDE PACING ARTIFACT DETECTION AMPLIFIER CIRCUIT WITH DRIVEN RIGHT LEG FOR FILTERING HIGH FREQUENCY NOISE CAUSED BY MULTIPLE NOISE SOURCES

[75] Inventor: John M. Kruse, Columbia Heights, Minn.

[73] Assignee: Medtronic, Inc., Minneapolis, Minn.

[21] Appl. No.: 133,539

[22] Filed: Oct. 7, 1993

[51] Int. Cl.⁶ ............................................ A61B 5/0452
[52] U.S. Cl. ...................................... 128/697; 607/27
[58] Field of Search ....................... 128/696, 697, 901; 607/9, 27; 318/801; 307/87

[56] References Cited

U.S. PATENT DOCUMENTS

| | | | |
|---|---|---|---|
| 161,529 | 11/1892 | Stotts et al. | 128/419 |
| 3,946,744 | 3/1976 | Auerbach | 128/419 |
| 4,226,245 | 10/1980 | Bennett, Jr. | 128/419 |
| 4,509,004 | 4/1985 | Shepard, Jr. | 318/801 |
| 4,630,204 | 12/1986 | Mortara | 128/901 |
| 5,111,059 | 5/1992 | Woodworth | 307/87 |
| 5,148,812 | 9/1992 | Verrier et al. | 128/704 |
| 5,217,010 | 6/1993 | Tsitlik et al. | 607/9 |

OTHER PUBLICATIONS

J. D. Webster, ed.: "*Medical Instrumentationn Applicaton and Design*," Houghton Mifflin Company, Boston, 1978.

*Primary Examiner*—George Manuel
*Attorney, Agent, or Firm*—Harold R. Patton

[57] ABSTRACT

A pacing artifact detection apparatus and method uses high speed operational amplifiers configured as an instrumentation amplifier to sense common mode noise signals at frequencies up to and above 10 MHz. The common mode noise signals are eliminated from a patient's pacing artifact signal by driving the noise signals back onto the body of the patient.

5 Claims, 5 Drawing Sheets

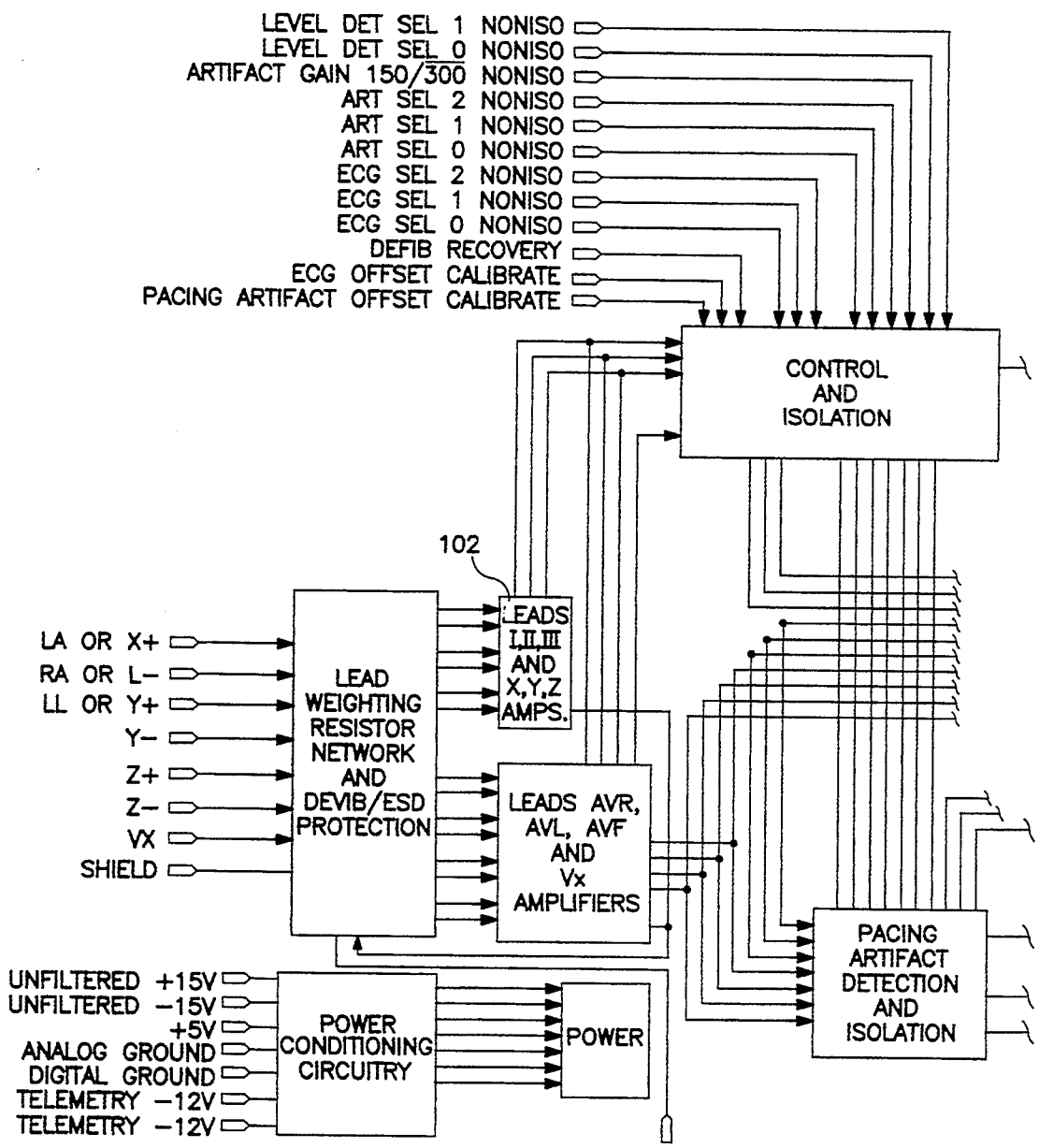
FIG. IA

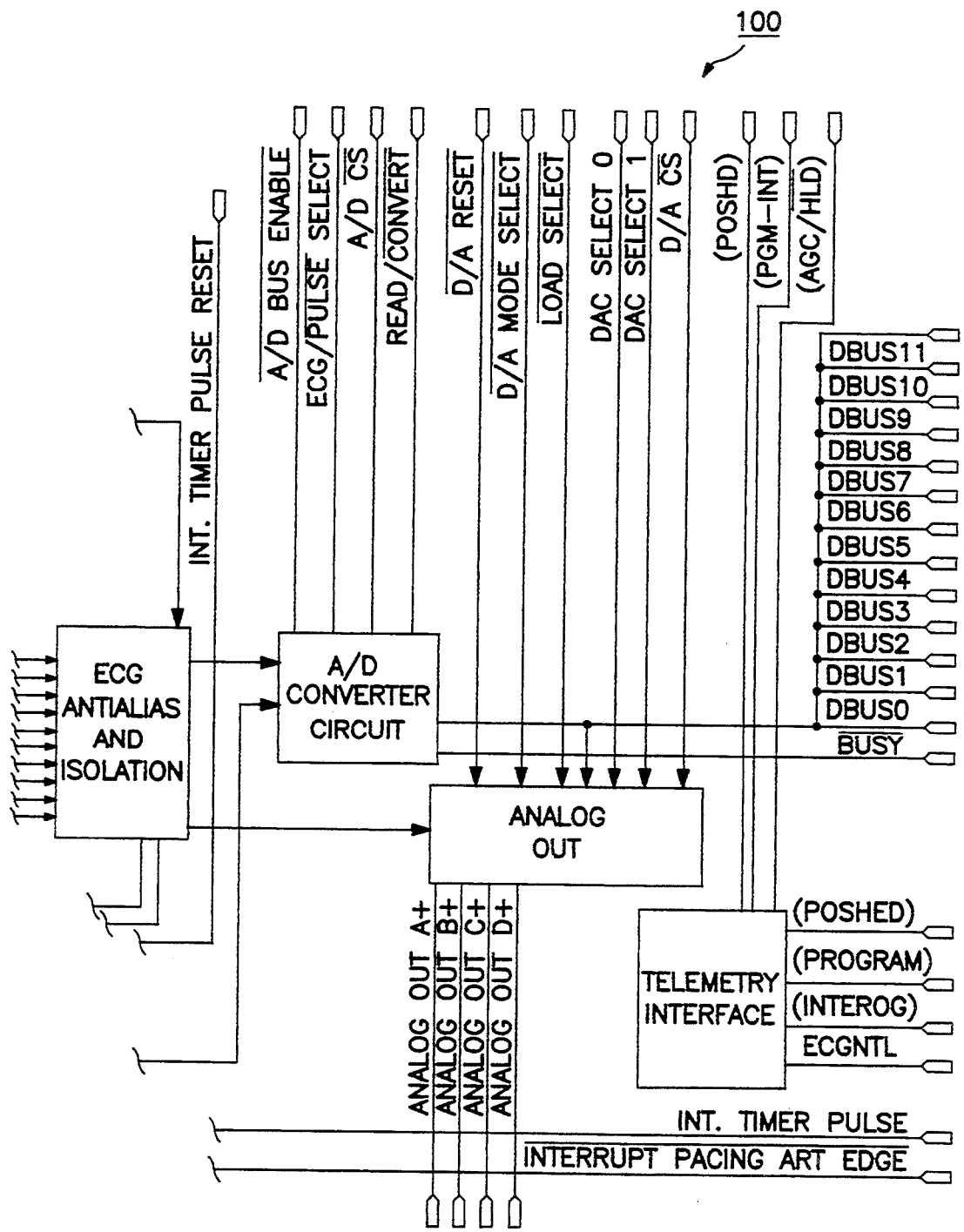
FIG. IB

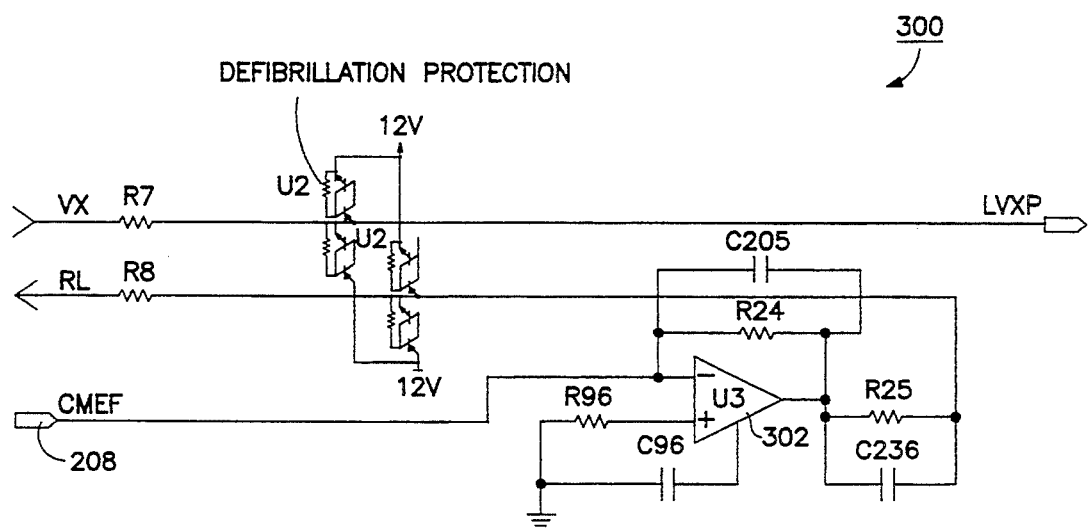
FIG. 3
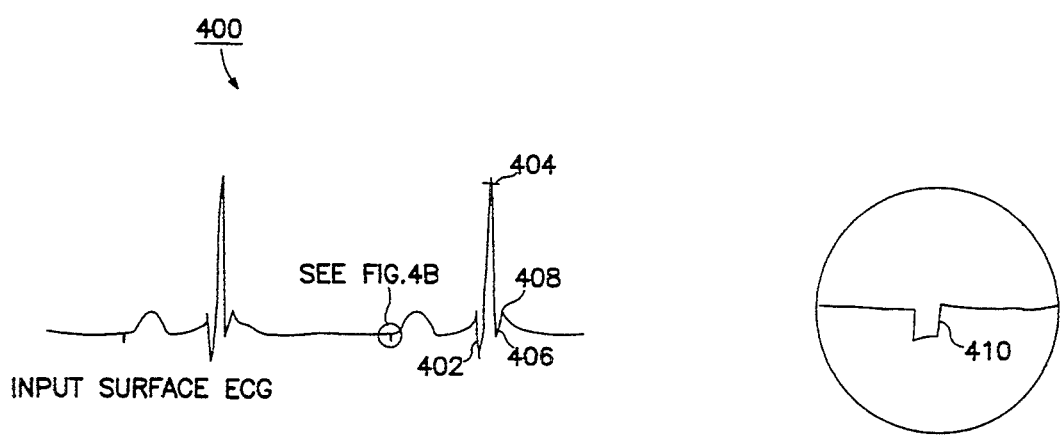
FIG. 4A
FIG. 4B

LOW AMPLITUDE PACING ARTIFACT DETECTION AMPLIFIER CIRCUIT WITH DRIVEN RIGHT LEG FOR FILTERING HIGH FREQUENCY NOISE CAUSED BY MULTIPLE NOISE SOURCES

BACKGROUND OF THE INVENTION

1. Field of the Invention

This invention relates generally to the field of medical monitoring devices, and more particularly relates to medical devices used to detect low amplitude artifacts produced by artificial cardiac pacing.

2. Description of the Prior Art

A wide variety of cardiac pacemakers are known and commercially available. Pacemakers are generally characterized by which chambers of the heart they are capable of sensing, the chambers to which they deliver pacing stimuli, and their responses, if any, to sensed intrinsic electrical cardiac activity. Some pacemakers deliver pacing stimuli at fixed, regular intervals without regard to naturally occurring cardiac activity. More commonly, however, pacemakers sense electrical cardiac activity in one or both of the chambers of the heart, and inhibit or trigger delivery of pacing stimuli to the heart based on the occurrence and recognition of sensed intrinsic electrical events. A so-called "SSI" pacemaker, for example, senses electrical cardiac activity in a chamber, atrium (A) or ventricle (V), of the patient's heart, and delivers pacing stimuli to the same chamber only in the absence of electrical signals indicative of natural chamber contractions. A "DDD" pacemaker, on the other hand, senses electrical signals in both the atrium and ventricle of the patient's heart, and delivers atrial pacing stimuli in the absence of signals indicative of natural atrial contractions, and ventricular pacing stimuli in the absence of signals indicative of natural ventricular contractions. The delivery of each pacing stimulus by a DDD pacemaker is synchronized with prior sensed or paced events.

Pacemakers are also known which respond to other types of physiological based signals, such as signals from sensors for measuring the pressure inside the patient's ventricle or measuring the level of the patient's physical activity. These devices are labeled "SSIR" for a single chamber version or "DDDR" for a dual chamber version.

As pacemaker technology as well as integrated circuit and lead technologies have evolved, chronic pacing thresholds have approached very low values (<<1.0 volts) and very efficient low current CMOS amplifier designs have become available. Instrumentation OP Amps for acquiring biopotential signals (ECG, EEG, EMG, etc.) as well as electrical signals produced by implantable devices such as cardiac pacemakers are now common in the art. Along with the development of such instrumentation OP Amps, the concepts associated with using a driven right leg system for canceling out 60 HZ common mode noise and noise from florescent lights have evolved.

U.S. Pat. No. 5,161,529, issued to Stotts et al. describes a circuit in which the frequency response of the sense amplifier is selectively set to detect cardiac activity in the form of the intrinsic QRS pattern, but which is switched to a lower frequency bandpass to render it more responsive to an evoked potential at the moment that a stimulating pulse is delivered to the heart.

U.S. Pat. No. 4,226,245, issued to Bennett, Jr. describes circuitry which is capable of distinguishing a pacing pulse from a patient's QRS wave in the presence of noise sources such as 60 HZ line noise or other noise sources having signal rise times in the millisecond range.

U.S. Pat. No. 3,946,744, issued to Auerbach describes circuitry utilizing a driven right leg electrode to eliminate common-mode noise generated by 60 Hz power line frequency as well as other pickup noise signals in a system which transmits pacing artifact information.

At times, however, the signal-to-noise ratio of electrical signals discussed hereinbefore, becomes too low for the prior art systems to adequately identify the high frequency pacing artifact, particularly when the pacing artifact's frequency spectrum lies near the middle of the spectrum of noise generated by multiple noise generators. What is needed is a system or device capable of canceling out high frequency noise caused by a multitude of noise sources, including but not limited to switched mode power supplies, DC/DC converters, and the noise generated by a pacemaker programming head, in addition to those noise sources discussed hereinbefore.

SUMMARY OF THE INVENTION

The present invention overcomes the disadvantages of the prior art systems by providing a method of and apparatus for monitoring expressly directed to allow accurate pacing artifact detection when the frequency spectrum of the pacing artifact lies in the middle of the spectrum of noise that is produced by multiple noise sources. This is accomplished by using high speed OP Amps configured as an instrumentation OP Amp with a driven right leg. The high speed OP Amps operate to cancel out the high frequency noise caused by a multitude of sources, including switched mode power supplies, DC/DC converters (10 KHZ to 10 MHZ), and the noise generated by a pacemaker programming head such as a Medtronic pacemaker programming head having a carrier frequency of 175 KHZ. The inventive circuit also rejects and cancels out common mode signals from other noise sources having frequencies above 10 MHZ.

Pacing artifact detection is accomplished at amplitudes several times smaller than previously known techniques. Because high speed OP Amps are used, power to the circuit can be supplied by a switched mode power supply. This is due to the high speed OP Amp supply ripple rejection at high frequencies and inherent ability to cancel out and reject radiated noise produced by switched mode power supplies.

The inventive apparatus operates by sampling a common mode signal taken at the outputs of two high speed OP Amps which serve as the input stage of a high speed instrumentation amplifier. This common mode signal is than fed into a driven right leg high speed Op Amp which inverts the common mode signal and drives the inverted common mode signal back onto the body of the patient, effectively canceling out the original common mode signal while not disturbing the differential signal.

The frequency at which the inventive circuit will fail to cancel out the common mode noise is limited only by the speed of the high speed OP Amps and the parasitic capacitance and inductance found in the various components in the circuit loop such as the cable, circuit board traces and the resistors in the circuit loop.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 1 is a block diagram illustrating one embodiment of a system for detecting low amplitude pacemaker pacing artifacts;

FIG. 3 is a schematic diagram illustrating one embodiment of a portion of the system depicted in FIG. 1, wherein there is shown a driven right leg high speed OP Amp for inverting the common mode signals associated with multiple noise sources and driving the inverted signals back onto the body of a patient;

FIG. 4 is a graphical representation of an EKG signal containing a pacing artifact.

DETAILED DESCRIPTION OF THE PREFERRED EMBODIMENT

Figure 2:
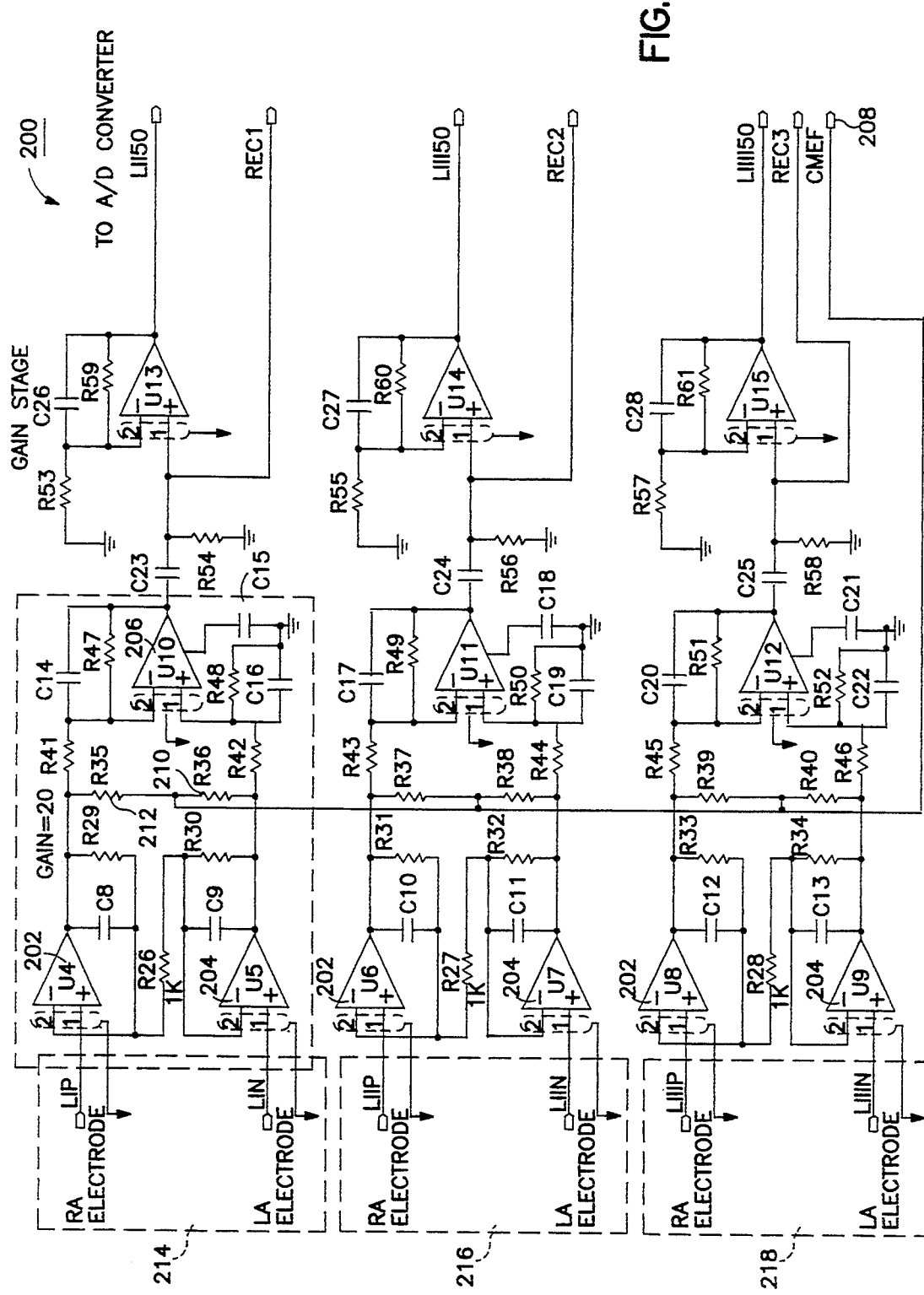
FIG. 2 is a schematic diagram illustrating one embodiment of a portion of the system depicted in FIG. 1, wherein there is shown multiple input channels, each channel including high speed OP Amp circuitry for sensing differential signals representative of pacing artifacts, and for sensing common mode signals associated with multiple noise sources.

FIG. 1 is a block diagram illustrating one embodiment of a system 100 for detecting low amplitude pacemaker pacing artifacts, wherein the pacing artifacts have a frequency spectrum which lies in the middle of a spectrum of noise produced by a plurality of noise sources. These noise sources include, but are not limited to noise generated from a pacemaker programming head having a carrier frequency of 175 kHz for example, and noise generated from a switched mode power supply having a frequency range from 10 kHz to 10 MHz for example. High speed OP Amps contained within instrumentation amplifier block 102 are configured to accurately detect such pacing artifacts, even in the presence of multiple noise sources discussed hereinbefore.

A graphical representation of an observed EKG signal containing a pacing artifact 410 is illustrated in FIG. 4. The electrical noise including muscle stimulating signals have been remove in this illustration to better depict the signals of interest. In FIG. 4, the most distinguishing feature is "R" wave 404 representing the electrical depolarization of a patient's ventricles. "Q" wave 402 depicts the atrial depolarization, and "S" and "T" waves 406 and 408 are associated with repolarization. It is important to note that pacing artifact 410 is ordinarily sensed as a lower amplitude and composed of much higher frequency components than "R" wave 404. This tends to make pacing artifact 410 difficult to monitor using prior art EKG monitoring devices, particularly where multiple noise sources are operating in a frequency spectrum identical to or nearly identical to the pacing artifact frequency spectrum.

Moving now to FIG. 2, there is illustrated a schematic diagram 200 showing one embodiment of a portion comprising the input stage of the present invention. Common mode noise rejection is minimized for the inventive apparatus by controlling the length, width, height, and distance of circuit board traces from the ground and power planes. In addition, the spacing between the circuit board traces is also controlled to minimize crosstalk. Specifically, the circuit traces associated with OP Amp 202 as well as OP Amp 302 in FIG. 3 are matched with their respective counterpart in all physical parameters to minimize impedance imbalances at high frequency using methods known to those skilled in the art. Matching the physical parameters increases the common mode rejection at high frequencies. Furthermore, the circuit traces associated with each leg of OP Amp 206 are also matched to maximize the common mode noise rejection.

Figure 5:
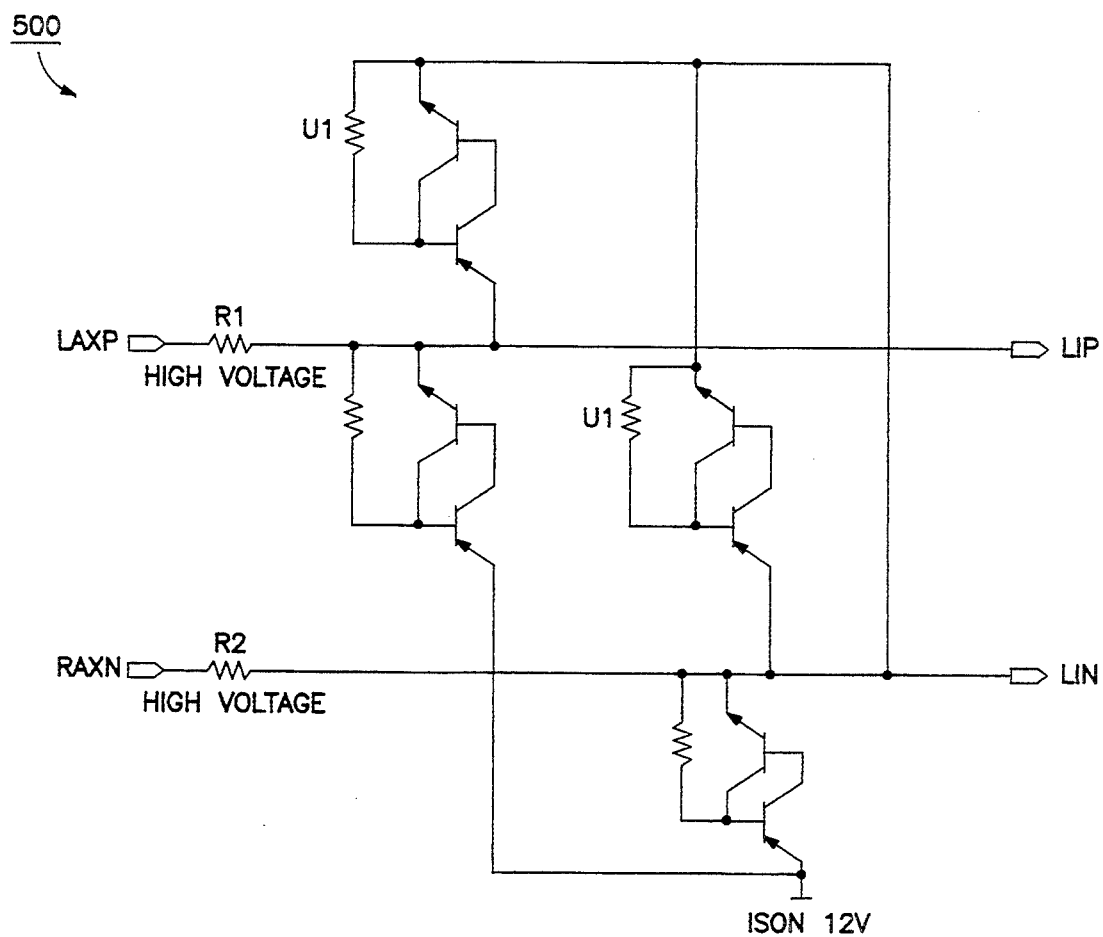
FIG. 5 is a schematic diagram illustrating one embodiment of a portion of the system depicted in FIG. 1, wherein preferred input protection circuitry is shown.

The present inventive apparatus requires that all parasitic capacitances be minimized so as not to adversely effect the signal integrity. In addition, it is also necessary that Op Amps 202 and 204 be protected from defibrillation and electro-static discharge energies. Therefore, in view of the foregoing, a means of protecting these sensitive inputs was needed that would not substantially add to the parasitic capacitances. The solution was achieved in the inventive apparatus using an SCR Array 500 to protect the inputs as illustrated in FIG. 5. The SCR Array 500 adds a minuscule 3 pf of capacitive loading to each input. Previous protection circuits, including, but not limited to, zener diodes, transorbs, and varistors, contribute 200 to 2000 pf of parasitic capacitance.

Looking again at FIG. 2, multiple input channels 214, 216 and 218 are shown. The operation of each input channel 214, 216 and 218 is identical. Therefore, the operation of the illustrated embodiment for that portion of the present invention will be discussed with reference to a single input channel 214. Looking again at FIG. 2, an input signal 400 similar to that depicted in FIG. 4, and containing a pacing artifact 410, is inputted into high speed, ultra-low noise, precision OP Amp 202 and high speed, ultralow noise, precision OP Amp 204. Op Amps 202 and 204 comprise the input stage of the instrumentation amplifier 102 illustrated in the functional embodiment 100 employing the present invention. These Op Amps, 202, 204, function to acquire low amplitude differential signals riding on high amplitude common mode noise signals even beyond 10 MHz, a feature not hereto before available in the art of pacing artifact detection. High speed, low noise video OP Amp 206 functions as the output stage of instrumentation amplifier 102.

The common mode multiple source noise signals desired to be eliminated are sampled across the outputs of OP Amps 202 and 204 which are common to the inputs of high speed output OP Amp 206. The sampling occurs at the junction where two precision matched resistors 210 and 212 are joined, and is introduced to associated driven right leg circuitry at output node 208. It is important to note that precision resistors 210 and 212 are selected to have parasitic capacitance and inductance characteristics to minimize any adverse effects on the overall operating speed of instrumentation amplifier 102. Moving now to FIG. 3, driven right leg circuit 300 functions to invert the sampled common mode noise signals presented at output node 208. The common mode noise signals are fed into driven right leg OP Amp 302, which first inverts the noise signals, then amplifies the noise signals, and finally drives the inverted common mode noise signals back onto the body of a patient. The overall effect of the present invention as depicted in the above embodiments, is to effectively cancel out the original common mode signal while simultaneously not disturbing the differential signal containing the desired pacing artifact.

The frequency at which the embodiments of the present invention will fail to cancel out the common mode noise is limited by the speed of OP Amps 202, 204, 302, and the parasitic capacitance and inductance found in the various components in the circuit loop between input circuit 200 and driven right leg circuit 300.' The embodiments presented hereinbefore detect pacing artifacts several times smaller than prior art techniques and offers several advantages not hereto before available such as the use of lighter weight and inexpensive switched mode power supplies as the power source for the circuitry. This is due to the ripple rejection at high frequencies and the ability of the high speed OP Amps 202, 204 and 302 to cancel out and reject the radiated noise produced by the power supply, a feature not recognized or disclosed by the prior art.

From the foregoing detailed descriptions of particular embodiments of the present invention, it should be apparent that a pacemaker pacing artifact detection apparatus has been disclosed which is provided with the capability of detecting pacing artifact signals at lower amplitudes hereto before available in the art of pacing artifact detection. Furthermore, the inventive apparatus rejects and cancels out common mode noise signals generated by multiple noise sources beyond frequencies of 10 MHz, a feature also not hereto before available in the art of pacing artifact detection.

While the invention has been described above in connection with a particular embodiment, one skilled in the art will appreciate that the invention is not necessarily so limited. It will thus be understood that numerous other embodiments, examples, uses, modifications of, and departures from the teachings disclosed may be made, without departing from the spirit and scope of the present invention as claimed herein.

I claim:

1. An apparatus for filtering high frequency noise signals having frequencies up to 10 MHz generated by a plurality of noise sources from EKG signals having high frequency, (RF) pacing artifacts, said apparatus comprising:

means for sensing said EKG signals having said pacing artifacts;

means coupled to said sensing means for amplifying frequencies up to 10 MHz within said EKG signals to produce amplified EKG signals;

means coupled to said amplifying means for generating common-mode noise signals including frequencies of up to 10 MHz, said common-mode noise signals comprising a portion of said amplified EKG signals.; and means coupled to said generating means for inverting said common-mode noise signals and means for driving said inverted common-mode noise signals back onto a body of a patient, whereby said pacing artifacts are preserved and said high frequency noise signals are canceled.

2. The apparatus of claim 1 wherein said means for amplifying said EKG signals comprises a plurality of high speed operational amplifiers.

3. The apparatus of claim 1 wherein said means for inverting said common mode noise signals comprises at least one high speed operational amplifier.

4. An apparatus for protecting high speed biopotential amplifiers from ESD and defibrillation energies without distorting EKG signal having a pacing artifact, said apparatus comprising:

(a) at least one high speed biopotential amplifier having at least one input and one output; and (b) at least one SCR array coupled to said input, said SCR array adding no more than about 3 picofarads of parasitic capacitance to said input.

5. A method for filtering high frequency noise signals having frequencies up to 10 MHz generated by a plurality of noise sources from EKG signals having high frequency, (RF), pacing artifacts, said method comprising the steps of:

sensing said EKG signals having said pacing artifacts from a patient's body.;

amplifying frequencies up to 10 MHz within said EKG signals to produce amplified EKG signals;

generating common-mode noise signals including frequencies of up to 10 MHz from said amplified EKG signals;

inverting said common-mode noise signals; and driving said inverted common-mode noise signals back onto said patient's body, whereby said high frequency noise signals are canceled and said pacing artifacts are preserved.

\* \* \* \* \*